US012648974B2

(12) United States Patent
    Tsai et al.

(10) Patent No.:  US 12,648,974 B2
(45) Date of Patent:      Jun. 9, 2026

(54) USE OF *LACTOBACILLUS PARACASEI* GM-080 FOR MODULATING IMMUNE FUNCTION

(71) Applicant: GenMont Biotech Incorporation, Tainan City (TW)

(72) Inventors: Wan-Hua Tsai, Kaohsiung City (TW); Wen-Wei Chang, Taichung City (TW); Chia-Hsuan Chou, Tainan City (TW); I-Jen Wang, New Taipei City (TW); Wen-Ling Yeh, Tainan City (TW); Jhih-Hua Jhong, Gongguan Township, Miaoli County (TW); Tzong-Yi Lee, Hsinchu City (TW)

(73) Assignee: GENMONT BIOTECH INCORPORATION, Tainan City (TW)

( * ) Notice: Subject to any disclaimer, the term of this patent is extended or adjusted under 35 U.S.C. 154(b) by 566 days.

(21) Appl. No.: 17/692,414

(22) Filed: Mar. 11, 2022

(65) Prior Publication Data

US 2023/0201279 A1      Jun. 29, 2023

(30) Foreign Application Priority Data

Dec. 27, 2021    (TW) ................................. 110148821

(51) Int. Cl.
    *A61K 35/747*        (2015.01)
    *A23L 33/00*         (2016.01)
    *A23L 33/135*        (2016.01)
    *A61P 37/08*         (2006.01)

(52) U.S. Cl.
    CPC .......... *A61K 35/747* (2013.01); *A23L 33/135* (2016.08); *A23L 33/40* (2016.08); *A61P 37/08* (2018.01); *A23V 2002/00* (2013.01); *A23V 2400/165* (2023.08)

(58) Field of Classification Search
    None
    See application file for complete search history.

(56) References Cited

U.S. PATENT DOCUMENTS

| | | | |
|---|---|---|---|
| 6,994,848 B2 * | 2/2006 | Hsu ........................ | C12N 1/205 |
| | | | 435/853 |
| 2023/0201279 A1 * | 6/2023 | Tsai ........................ | A23L 33/40 |
| | | | 424/780 |

OTHER PUBLICATIONS

Levin et al. "Toxicity of Oligodeoxynucleotide Therapeutic Agents", chapter 5; In: "Antisense Research and Application", 1998, pp. 169-170.*

Wickstrom et al. "Strategies for administering targeted therapeutic oligodeoxynucleotides". Trends in biotechnology, 1992, vol. 10, No. 8, pp. 281-287.*

Schelermann et al. "Clinical evaluation of CpG oligonucleotides as adjuvants for vaccines targeting infectious diseases and cancer". Vaccine. 2014, 32 (48), pp. 6377-6389.*

* cited by examiner

*Primary Examiner* — Vera Afremova
(74) *Attorney, Agent, or Firm* — MUNCY, GEISSLER, OLDS & LOWE, P.C.

(57)                    ABSTRACT

The invention provides an extracellular vesicle and a nucleotide fragment isolated from *Lactobacillus paracasei* GM-080 with the deposition number BCRC 910220 and CCTCC M 204012 and use thereof. The invention also relates to a method for modulating immune function comprising administering a composition including the extracellular vesicle and the nucleotide fragment.

2 Claims, 10 Drawing Sheets
(1 of 10 Drawing Sheet(s) Filed in Color)

Specification includes a Sequence Listing.

INFORMATION STORAGE AND PROCESSING

Translation, ribosomal structure and biogenesis

Replication, recombination and repair

Transcription

CELLULAR PROCESSES AND SIGNALING

Cell cycle control, cell division, chromosome partitioning

Defense mechanisms

Signal transduction mechanisms

Cell wall/membrane/envelope biogenesis

Cell motility

Intracellular trafficking, secretion, and vesicular transport

Post-translational modification, protein turnover, and chaperones

METABOLISM

Energy production and conversion

Carbohydrate transport and metabolism

Amino acid transport and metabolism

Nucleotide transport and metabolism

Coenzyme transport and metabolism

Lipid transport and metabolism

Inorganic ion transport and metabolism

Secondary metabolites biosynthesis, transport, and catabolism

POORLY CHARACTERIZED

Function unknown

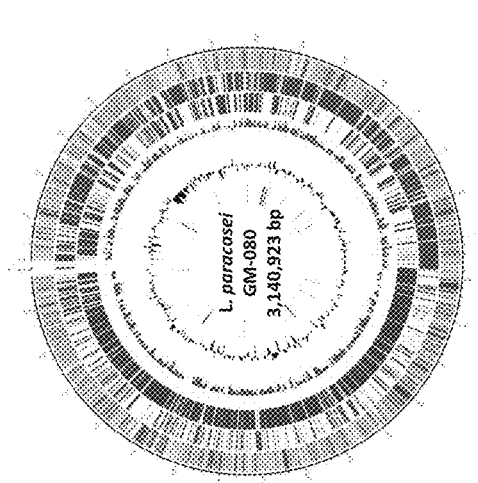

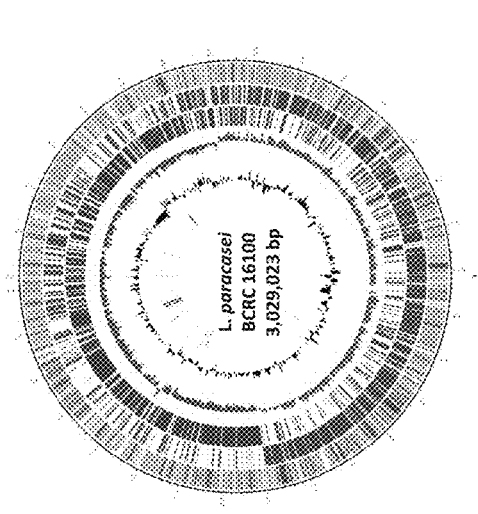

FIG. 1

USE OF *LACTOBACILLUS PARACASEI* GM-080 FOR MODULATING IMMUNE FUNCTION

The instant application contains a Sequence Listing which has been submitted electronically in the ASCII text file and is hereby incorporated by reference in its entirety. The ASCII text file is a sequence listing entitled "2022-05-16-Seq-Listing" created on May 16, 2022 and having a size of 3,437 bytes in compliance of 37 CFR 1.821.

BACKGROUND OF THE INVENTION

Field of Invention

The invention relates to probiotics, and more particularly to the technical field of using an extracellular vesicle or a nucleotide fragment of *Lactobacillus paracasei* for modulating immune function.

Related Art

Allergy is a reaction caused by an abnormal immune system, it is a phenomenon in which the immune system triggers an overreacted immune response to harmless substances in the environment. Common allergic symptoms include swelling, tearing, itchy skin, eyes and nose, tachypnea, runny nose and dry skin, etc.

When an allergic reaction occurs, patients often use antihistamines and other allergy drugs to relieve allergic symptoms. However, allergy drugs generally have certain side effects. Therefore, how to use natural substances to modulate immune function to reduce allergic symptoms caused by overreaction of the immune system has always been the focus of the industry and academia.

Bacteria have certain nucleic acid substances called immunostimulatory sequence oligodeoxy nucleotides (ISS-ODNs) that can cause immune responses. At present, studies have found that immunostimulatory sequence oligodeoxy nucleotides (ISS-ODNs) can induce innate immune responses via TLR9, including stimulating NK cells to secrete IFN-α and IFN-γ and stimulating B cells or NK cells to activate. The currently known sequences of ISS-ODNs include TTAGGG, TTTCGTTT, TCAAGCTTGA, GAC-GATCGTC and ACGACGTCGT.

In addition, scholars or practitioners are using probiotics to modulate immune function and to fight allergies currently. However, not all probiotics have the function of modulating immune function, and the efficacy of probiotics with this function is not consistent. Therefore, finding probiotics or their metabolites and derivatives that have the efficacy to regulate immunocompetence and can be used for fighting allergies has always been the focus of research and development in the technical field to which the invention pertains, and it is also the subject to be solved by the invention.

SUMMARY OF THE INVENTION

An object of the invention is to provide a use of *Lactobacillus paracasei* GM-080 for preparing a pharmaceutical composition for modulating immune function comprising using an extracellular vesicle of the *Lactobacillus paracasei* GM-080 as an active ingredient for modulating immune function; wherein a preparation method of the extracellular vesicle comprises: after removing bacterial cells from a culture broth of the *Lactobacillus paracasei* GM-080, isolating the extracellular vesicle by concentration with a 100 kDa NMWL (nominal molecular weight limit) ultrafiltration membrane or a separation tool with an equivalent efficacy; wherein the deposition number of the *Lactobacillus paracasei* GM-080 is BCRC 910220 or CCTCC M 204012.

In order to achieve the aforementioned object of the invention, wherein the modulating immune function is anti-allergic.

In order to achieve the aforementioned object of the invention, wherein the modulating immune function is anti-inflammatory.

The invention further provides a use of a nucleotide fragment for preparing a pharmaceutical composition for modulating immune function, wherein a sequence of the nucleotide fragment comprises SEQ ID NO. 7, SEQ ID NO. 10, SEQ ID NO. 14, SEQ ID NO. 15, SEQ ID NO. 16, SEQ ID NO. 17 or SEQ ID NO. 18.

In order to achieve the aforementioned object of the invention, wherein the modulating immune function is anti-allergic.

In order to achieve the aforementioned object of the invention, wherein the modulating immune function is anti-inflammatory.

The invention further provides an extracellular vesicle of *Lactobacillus paracasei* GM-080, wherein a preparation method of the extracellular vesicle comprises: after removing bacterial cells from a culture broth of the *Lactobacillus paracasei* GM-080, isolating the extracellular vesicle by concentration with a 100 kDa NMWL (nominal molecular weight limit) ultrafiltration membrane or a separation tool with an equivalent efficacy; wherein the deposition number of the *Lactobacillus paracasei* GM-080 is BCRC 910220 or CCTCC M 204012.

The invention further provides a nucleotide sequence capable of modulate immune function comprising SEQ ID NO. 7, SEQ ID NO. 10, SEQ ID NO. 14, SEQ ID NO. 15, SEQ ID NO. 16, SEQ ID NO. 17 or SEQ ID NO. 18.

The invention further provides a composition for modulating immune function comprising an extracellular vesicle or a nucleotide fragment; wherein the extracellular vesicle comprises the aforementioned extracellular vesicle; wherein a sequence of the nucleotide fragment comprises SEQ ID NO. 7, SEQ ID NO. 10, SEQ ID NO. 14, SEQ ID NO. 15, SEQ ID NO. 16, SEQ ID NO. 17 or SEQ ID NO. 18.

In order to achieve the aforementioned object of the invention, wherein the composition is a pharmaceutical composition, a nutritional supplement or a health food.

In order to achieve the aforementioned object of the invention, wherein the composition can further comprise a pharmaceutically acceptable vehicle.

In order to achieve the aforementioned object of the invention, wherein the composition is a solution, a suspension, a emulsion, a powder, a tablet, a pill, a syrup, a lozenge, a troche, a chewing gum, a jatex or a capsule.

In order to achieve the aforementioned object of the invention, wherein the composition can further comprise an edible material; wherein the edible material comprises, but is not limited to water, fluid milk products, milk, concentrated milk, yogurt, sour milk, frozen yogurt, lactic acid bacteria-fermented beverages, milk powder, ice cream, cream cheeses, dry cheeses, soybean milk, fermented soybean milk, vegetable-fruit juices, fruit juices, sports drinks, confectionery, jellies, candies, infant formulas, health foods, animal feeds, Chinese medicinal herbs or dietary supplements.

In summary, among the many types of *Lactobacillus paracasei*, the *Lactobacillus paracasei* GM-080 provided by the invention has a relatively better ability for modulating immune function, the extracellular vesicle thereof further has an efficacy of stimulating the secretion of IFN-γ and IL-12, which is beneficial to suppress allergic reactions. In addition, the invention further provides several types of the nucleotide fragment that can be used to regulate immuno-competence, including anti-inflammatory and anti-allergic nucleotide fragments, the nucleotide fragment also has an efficacy of stimulating the secretion of IFN-γ and IL-12, and is very suitable for using in the research and preparation of anti-inflammatory or anti-allergic compositions to promote the development of the industry and provide another option for modulating immune function.

These features and advantages of the invention will be fully understood and appreciated from the following detailed description of the accompanying drawings.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 1 is whole genome maps and genetic characteristics of *Lactobacillus paracasei* GM-080 and *Lactobacillus paracasei* BCRC 16100;

DETAILED DESCRIPTION OF THE INVENTION

Figure 2:
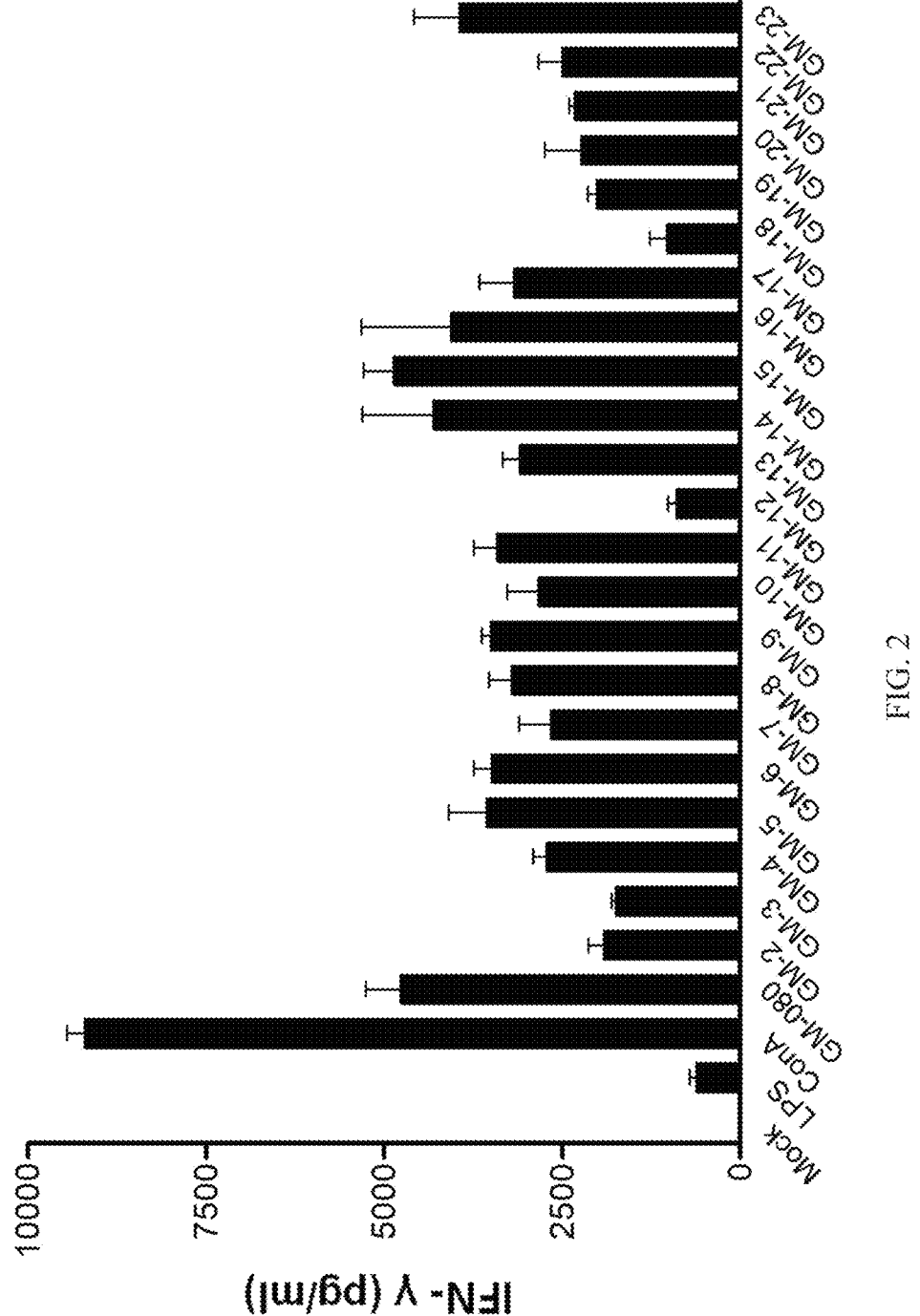
FIG. 2 is results of an ability of 23 different strains of *Lactobacillus paracasei* in stimulating IFN-γ secretion.

All the technical and scientific terms mentioned in the specification are meanings that can be commonly understood by a person having ordinary in the art to which the invention pertains unless otherwise defined.

The singular terms "a", "an", "one", "the" described in the specification and claims can refer to more than one subject unless otherwise indicated.

The "or", "and", and "as well as" used in the specification refer to "or/and" unless otherwise specified. In addition, the terms "contain", "include" and "comprise" are not restrictive open-ended conjunctions. "The foregoing paragraph" is only a systematic reference and should not be construed as limiting the subject of the invention.

The term "modulate immune function" and similar terms in the specification refers to the ability to increase or decrease immune response specifically or non-specifically, and also refers to suppress allergic reaction or autoimmune response, but at the same time retain or even enhance the effect in resisting or fighting foreign invaders or cancer cells.

The terms "anti", "inhibit", "suppress" and similar terms refer to preventing, delaying, retarding, improving, reducing or reversing the occurrence of symptoms.

The term "pharmaceutically acceptable" means that a substance or a composition must be compatible with a composition provided by the invention, in which an active ingredient or a composition provided in the invention and at least one pharmaceutically acceptable vehicle are used to prepare a dosage form suitable for the composition of the invention by using techniques well known to a person having ordinary in the art to which the invention pertains. Wherein the dosage form includes, but is not limited to, solution, emulsion, suspension, powder, tablet, lozenge, troche, chewing gum, capsule and other similar dosage forms suitable for the invention.

The term "pharmaceutically acceptable vehicle" comprises one ingredient form or more than one ingredient form selected from the following: solvent, emulsifier, suspending agent, decomposing agent, binder, excipient, stabilizer, chelating agent, diluent, gellant, preservative, lubricant, surfactant, and other similar vehicles suitable for the invention.

In the aforementioned composition, one or more of dissolution adjuvant, buffer, coloring agent, flavoring agent commonly used in the preparation field can also be appropriately added as needed.

The term "pharmaceutically acceptable excipient" comprises, but is not limited to, at least one of polymer, resin, plasticizer, filler, lubricant, diluent, binder, disintegrant, solvent, co-solvent, surfactant, preservative, sweetener, flavoring agent, pharmaceutical grade dye or pigment, and viscosity agent.

The term "pharmaceutical composition" refers to a solid or liquid composition whose form, concentration and purity are suitable for administration to a patient, after administration, it can induce desired physiological changes; the pharmaceutical composition is sterile and/or non-pyrogenic.

The term "effective amount" refers to a dose required to produce or cause the expected biological response, and is not quantified as needed for treatment and recovery. A person having ordinary in the art to which the invention pertains can understand that an effective amount of the pharmaceutical composition can vary depending on the following factors such as: expected biological end point, biological active agent to be delivered, composition of encapsulating matrix, target tissue, etc.

The materials used in the invention, unless otherwise specified, are all commercially available materials that can be easily obtained. The *Lactobacillus paracasei* GM-080 used in the embodiments of the invention is deposited at Taiwan Food Industry Research and Development Institute (FIRDI) with the deposition number BCRC 910220 and China Center for Type Culture Collection (CCTCC) with the deposition number CCTCC M 204012.

*Lactobacillus paracasei* strains except the *Lactobacillus paracasei* GM-080 (GM-080 for short) used in the embodiments of the invention are used as comparative examples. These strains (BCRC 16100, GM-2, GM-3, GM-4, GM-5, GM-6, GM-7, GM-8, GM-9, GM-10, GM-11, GM-12, GM-13, GM-14, GM-15, GM-16, GM-17, GM-18, GM-19, GM-20, GM-21, GM-22, GM-23, L9, HD1.7 and Lpc10)

should not be used as a basis for judging whether the invention can be implemented. If necessary, *Lactobacillus paracasei* strains that are commercially available or can be obtained by any other means can also be used to replace these strains. Replacing these strains (BCRC 16100, GM-2, GM-3, GM-4, GM-5, GM-6, GM-7, GM-8, GM-9, GM-10, GM-11, GM-12, GM-13, GM-14, GM-15, GM-16, GM-17, GM-18, GM-19, GM-20, GM-21, GM-22, GM-23, L9, HD1.7 and Lpc10) with *Lactobacillus paracasei* strains that are commercially available or can be obtained by any other means as comparative examples will not affect the implementation of the invention.

The novel technical features of the invention, including specific features, are disclosed in the claims of the invention. For the technical features of the invention, a better understanding can be achieved in conjunction with the embodiments, drawings, and detailed description in the specification based on the principles of the invention.

The invention is exemplified and illustrated by the following embodiments, but the invention is not limited by the following embodiments.

Embodiment 1: Whole Genome Sequencing and Analysis of the *Lactobacillus paracasei* GM-080

Whole genome sequencing and analysis of the *Lactobacillus paracasei* GM-080 (abbreviated as GM-080) were performed, and *Lactobacillus paracasei* BCRC 16100 (abbreviated as BCRC 16100) was used as a comparative example. The specific method is as follows. The genomic DNA of the two strains were extracted using the commercially available kit (QIAGEN; Cat. No. 69504), respectively, and then the whole genomes were sequenced using the Illumina Hiseq 2000 next-generation sequencer and Oxford Nanopore GridION third-generation sequencer. Subsequently, the sequencing results were multiply aligned with the gene database (multiple sequence alignment) and subjected to functional analysis, including comparison with the KEGG Pathway database. Moreover, the sequencing results were further aligned to the known immunostimulatory sequence oligodeoxynucleotides (ISS-ODNs) sequence. *Lactobacillus paracasei* L9, HD1.7 and Lpc10 mentioned in the publication (Zakie et. al. in 2020) were used as comparative examples. The gene annotations were produced with several tools, including: using Prokka to predict the whole genomic genes of prokaryotes (comprise protein coding and non-coding regions), using PlasFlow for plasmid identification, using the PHASTER tool to screen phage segments in the genome, and using BAGEL4 and CARD to respectively predict genes related to bacteriocin production and possible regions of drug resistance; also, regions may encode functional proteins were annotated and functionally classified by the eggNOG tool and combined with the Cluster of Orthologous Genes (COG) of the protein database.

The results are shown in FIG. 1 and Tables 1 to 5. FIG. 1 and Table 1 show that the genome sizes of GM-080 and BCRC 16100 are 3140923 bp and 3029023 bp, respectively. Their genetic information is shown in Table 1, GM-080 and BCRC 16100 belong to the same species, so the overall genetic information is similar, but still has some difference.

TABLE 1

|  | GM-080 | BCRC 16100 |
| --- | --- | --- |
| Size ( bp) | 3,140,923 | 3,029,023 |
| G + C content (%) | 46.3 | 46.4 |
| Total genes | 3,172 | 2,902 |
| Coding content (%) | 88.82 | 85.88 |
| Gene average length (bp) | 853 | 896 |
| Genes assigned to COGs | 2,548 (80.3%) | 2,387 (82.2%) |
| Chromosome | 1 | 1 |
| rRNA operons | 5 | 5 |
| tRNA | 62 | 62 |
| plasmids | 0 | 0 |
| Transposases | 69 | 13 |
| CRISPR loci | 1 | 2 |
| Prophage-like clusters | 6 | 0 |
| Bacteriocin | 1 | 2 |

According to the results of KEGG Pathway analysis (Table 2 and Table 3), GM-080 has unique genes related to the cell wall/cell membrane/envelope biosynthesis pathway (M), such as RFBP (exopolysaccharide biosynthesis polyprenyl glycosyl phosphotransferase), which is a gene related to the biosynthesis of extracellular polysaccharides (EPS). In addition, GM-080 has unique genes related to post-translational modification, protein turnover and molecular chaperone protein (0), such as GST (Glutathione 5-transferase).

TABLE 2

| Comparison of functional genes between GM-080 and BCRC 16100 | | | |
| --- | --- | --- | --- |
| KEGG Pathway | Same number of genes | Unique genes of GM-080 | Unique genes of BCRC 16100 |
| Cell wall/membrane/envelope biogenesis (M) | 81 | LYSA2 ' RFBP ' CPSJ ' WEFI ' WCHF ' AMSB ' LYTA (7) | DAPA ' KDSD ' CAPM ' RGPB ' BMUL 2606 ' TUAG ' MNAA ' GTF1 (8) |
| Post-translational modification, protein turnover, and chaperones (O) | 52 | GST (1) | |
| Carbohydrate transport and metabolism (G) | 158 | AGAD ' SP_0324 ' AGAV ' KDUI ' KDGK ' FOSD ' XYLP ' LACG (8) | YBBF ' MANZ ' BL01774 ' BMUL_6106 ' SP_2036 ' GATA2 ' GATC2 (7) |
| Amino acid transport and metabolism (E) | 139 | DPPA ' FRVX ' GLOA (3) | ABGB ' FBPC (2) |
| Coenzyme transport and metabolism (H) | 37 | | PDXA (1) |

TABLE 2-continued

| | Same number of genes | Unique genes of GM-080 | Unique genes of BCRC 16100 |
|---|---|---|---|
| | | Comparison of functional genes between GM-080 and BCRC 16100 | |
| KEGG Pathway | | | |
| Inorganic ion transport and metabolism (P) | 83 | | KDGT ' THIP (2) |
| Secondary metabolites biosynthesis, transport, and catabolism (Q) | 10 | | ADC ' OCAR 7510 (2) |
| Intracellular trafficking, secretion, and vesicular transport (U) | 13 | GBS0396 ' GBS0402 (2) | SECY2 ' SECA2 (2) |

TABLE 3

| KEGG pathway | Predicted gene name | KEGG NOG annot * |
|---|---|---|
| | | GM-080 unique genes list and simple function description |
| M | RFBP | exopolysaccharide, biosynthesis polyprenyl glycosylphosphotransferase |
| | CPSJ | Glycosyl Transferase |
| | WEFI | Glycosyl transferase (Group 1) |
| | WCHF | Glycosyl transferase (Group 1) |
| | AMSB | Glycosyl transferase, family 2 |
| | LYSA2 | endopeptidase |
| | LYTA | n-acetylmuramoyl-l-alanine amidase |
| O | GST | Glutathione S-transferase |
| G | AGAD | PTS System |
| | SP_0324 | iic component |
| | AGAV | PTS System |
| | KDUI | 4-deoxy-L-threo-5-hexosulose-uronate ketol-isomerase |
| | KDGK | pfkb domain protein |
| | FOSD | PTS system mannose fructose sorbose family IID compo-nent |
| | XYLP | Endo-1,4-beta-xylanase |
| | LACG | Glycosyl hydrolase family 1 |
| E | DPPA | Peptidase M55 D-aminopeptidase |
| | FRVX | Peptidase m42 family protein |
| | GLOA | glyoxalase bleomycin resistance protein dioxygenase |
| U | GBS0396 | Pfam: TraG |
| | GBS0402 | Inherit from COG: type IV secretion system protein |

*KEGG (Kyoto Encyclopedia of Genes and Genomes,); NOG-eggNOG (evolutionary genealogy of genes: Non-supervised Orthologous Groups)

The ISS-ODNs sequence alignment results are shown in Table 4. The occurrence frequencies of the 5 ISS-ODNs sequences in GM-080 are higher than the other 4 strains, especially TTAGGG (code: IM1) and TTTCGTTT (code: IM2). In addition, the genomes of GM-080 and BCRC 16100 not only comprise the 5 ISS-ODNs sequences described in Table 4, but also comprise sequences which are different from the 5 ISS-ODNs sequences (Table 5), respectively:

(1) The genomes of GM-080 and BCRC 16100 respectively have 4 different sequences which contain sequence IM3, as a core sequence. These sequences are differences in the first 4 to 6 nucleotides at the 5'end and 4 to 6 nucleotides at the 3'end., so are named as IM4, IM5, IM6, IM7 (found in the GM-080 genome), and IM8, IM9, IM 10, IM11 (found in the BCRC 16100 genome) herein;

(2) The genomes of GM-080 and BCRC 16100 respectively have 1 sequence and 3 sequences which contain sequence ODN2216, as a core sequence. These sequences are differences in the first 4 to 6 nucleotides at the 5'end and 4 to 6 nucleotides at the 3'end, so are named as ODN1 (found in the GM-080 genome), and ODN3, ODN4, ODN5 (found in the BCRC 16100 genome); and (3) The genomes of GM-080 and BCRC 16100 respectively have 1 sequence which contains sequence ODN2336, as a core sequence. These sequences are differences in the first 4 to 6 nucleotides at the 5'end and 4 to 6 nucleotides at the 3'end, so are named as ODN2 (found in the GM-080 genome), and ODN6 (found in the

TABLE 4

Occurrence frequencies of 5 ISS-ODNs sequences in the different
*Lactobacillus paracasei* strains

| | | | | Strain | Comparative example | | | |
|---|---|---|---|---|---|---|---|---|
| Code | SEQ ID NO. | sequence | Genome size (bp) | GM-080 3,140,923 | BCRC 16100 3,029,023 | L9 3,076,440 | HD1.7 3,039,280 | Lpc10 3,052,120 |
| IM1 | 1 | TTAGGG | frequency no. copies per $10^6$ bases | 292 93 | 276 91.1 | 187 60.8 | 184 60.5 | 193 63.2 |
| IM2 | 2 | TTTCGTTT | frequency no. copies per $10^6$ bases | 103 32.8 | 78 25.8 | 54 17.6 | 52 17.1 | 59 19.3 |
| IM3 | 3 | TCAAGCTTGA | frequency no. copies per $10^6$ bases | 4 1.3 | 4 1.3 | 3 1.0 | 2 0.7 | 3 1.0 |
| ODN2216 | 4 | GACGATCGTC | frequency no. copies per $10^6$ bases | 1 0.3 | 3 1 | ND ND | ND ND | ND ND |
| ODN2336 | 5 | ACGACGTCGT | frequency no. copies per $10^6$ bases | 1 0.3 | 1 0.3 | ND ND | ND ND | ND ND |

TABLE 5

ISS-ODNs sequence of GM-080 and BCRC 16100

| Code | SEQ ID NO. | Core sequence | Strain | Sequence |
|---|---|---|---|---|
| IM4 | 6 | TCAAGCTTGA | GM-080 | CAAGCGTCAAGCTTGAATGA |
| IM5 | 7 | | GM-080 | AAAAATTCAAGCTTGATAGT |
| IM6 | 8 | | GM-080 | CCATCGTCAAGCTTGACTTG |
| IM7 | 9 | | GM-080 | CCCTAATCAAGCTTGATTAA |
| IM8 | 10 | | BCRC 16100 | GCAGCTTCAAGCTTGAAAAA |
| IM9 | 11 | | BCRC 16100 | CCGGCCTCAAGCTTGAATTG |
| IM10 | 12 | | BCRC 16100 | TTTCATTCAAGCTTGACGCT |
| IM11 | 13 | | BCRC 16100 | CCTTAATCAAGCTTGATTAG |
| ODN1 | 14 | GACGATCGTC | GM-080 | GCTTGACGATCGTCTCTGGA |
| ODN2 | 15 | ACGACGTCGT | GM-080 | GGTCACGACGTCGTTTACAAA |
| ODN3 | 16 | GACGATCGTC | BCRC 16100 | AATTGACGATCGTCTAATTC |
| ODN4 | 17 | GACGATCGTC | BCRC 16100 | TGTCGACGATCGTCGTCTGT |
| ODN5 | 18 | GACGATCGTC | BCRC 16100 | CAGAGACGATCGTCAAGCGA |
| ODN6 | 19 | ACGACGTCGT | BCRC 16100 | CGTCACGACGTCGTGACCGGC |

Embodiment 2: Analysis of the Ability of the *Lactobacillus paracasei* GM-080 in Modulating Immune Function The mouse spleen was dissociated into single-cell suspensions of spleen cells based on the conventional method. The spleen cells were added into a 96-well plate (100 μl per well) at a concentration of $4 \times 10^6$ cells/ml, and then the GM-080 bacterial solution was added into the 96-well plate (100 μl per well) at a concentration of $4 \times 10^6$ cfu/well (that is, $2 \times 10^7$ cfu/ml). 22 other strains of *Lactobacillus paracasei* (GM-2, GM-3, GM-4, GM-5, GM-6, GM-7, GM-8, GM-9, GM-10, GM-11, GM-12, GM-13, GM-14, GM-15, GM-16, GM-17, GM-18, GM-19, GM-20, GM-21, GM-22, GM-23) were used as comparative examples, 100 μl of culture medium was used as the blank control group (mock), 100 μl of 2 μg/ml LPS (lipopolysaccharide) was used as a positive control group-1, and 100 μl of 4 μg/ml conA (concanavalin A) is used as a positive control group-2. After 48 hours of cultivation, the treated spleen cells were centrifuged and the supernatants were collected for IFN-γ and IL-12 analysis using the commercially available kits (BD OptEIA™ Mouse IFN-γ ELISA Set, Cat: 555138; BD OptEIA™ Mouse IL-12 (p70) ELISA Set, Cat: 555256).

Figure 3:
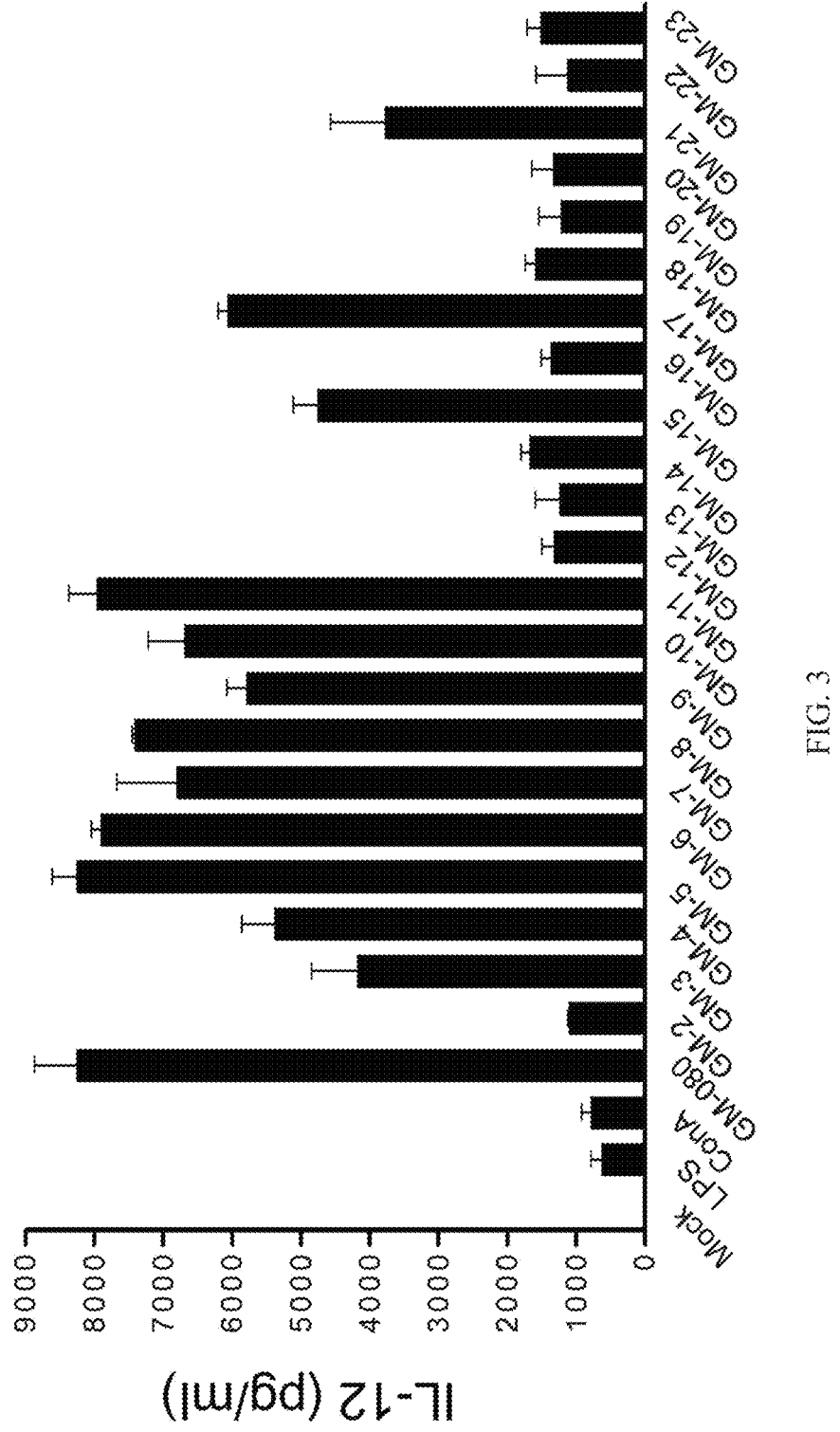
FIG. 3 is results of an ability of 23 different strains of *Lactobacillus paracasei* in stimulating IL-12 secretion.
Figure 4:
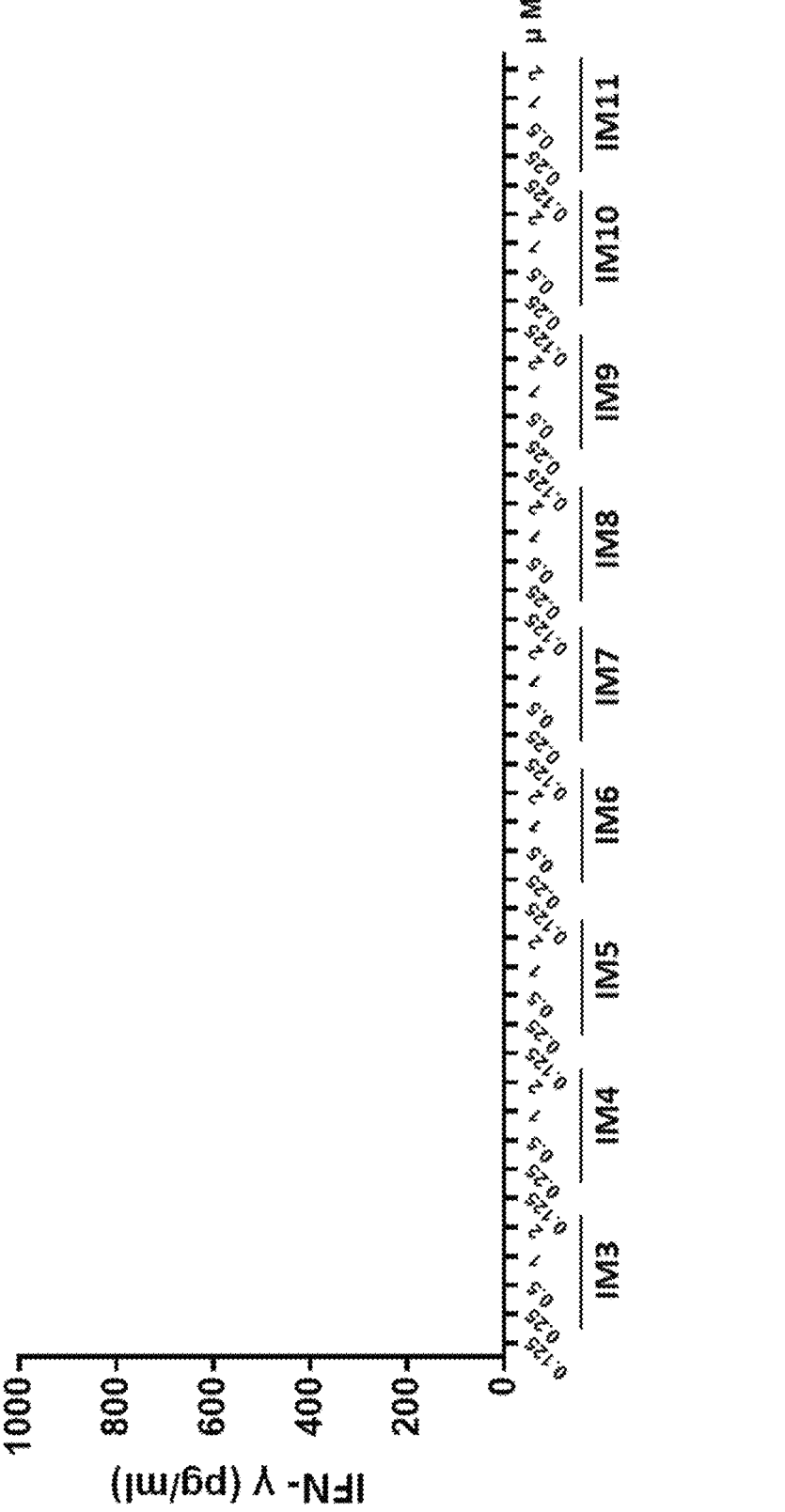
FIG. 4 and FIG. 5 are results of an ability of a nucleotide fragment including a nucleotide sequence of SEQ ID NO. 3 or SEQ ID NO. 6 to 19 in stimulating IFN-γ secretion.
Figure 5:
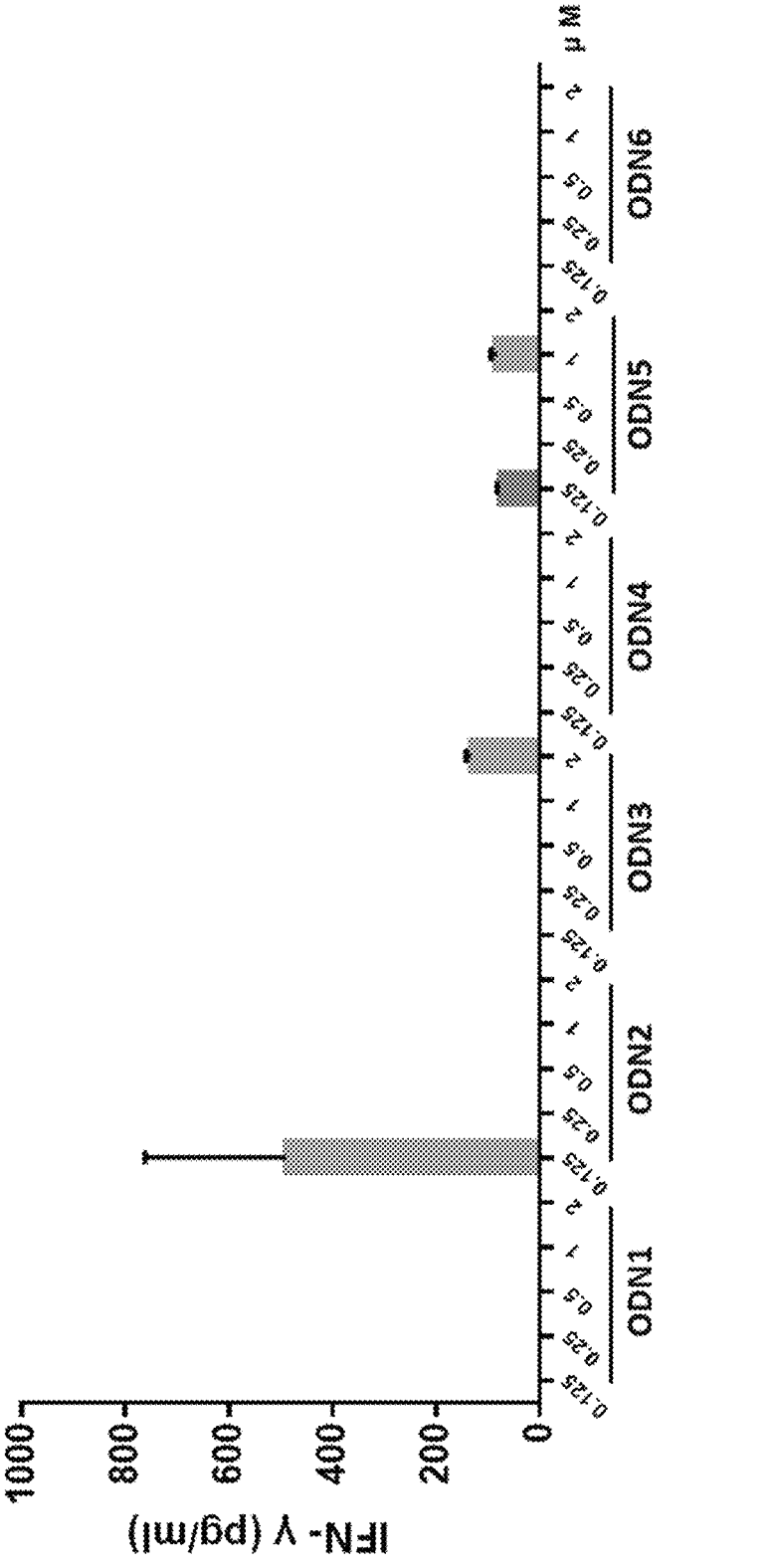
Figure 6:
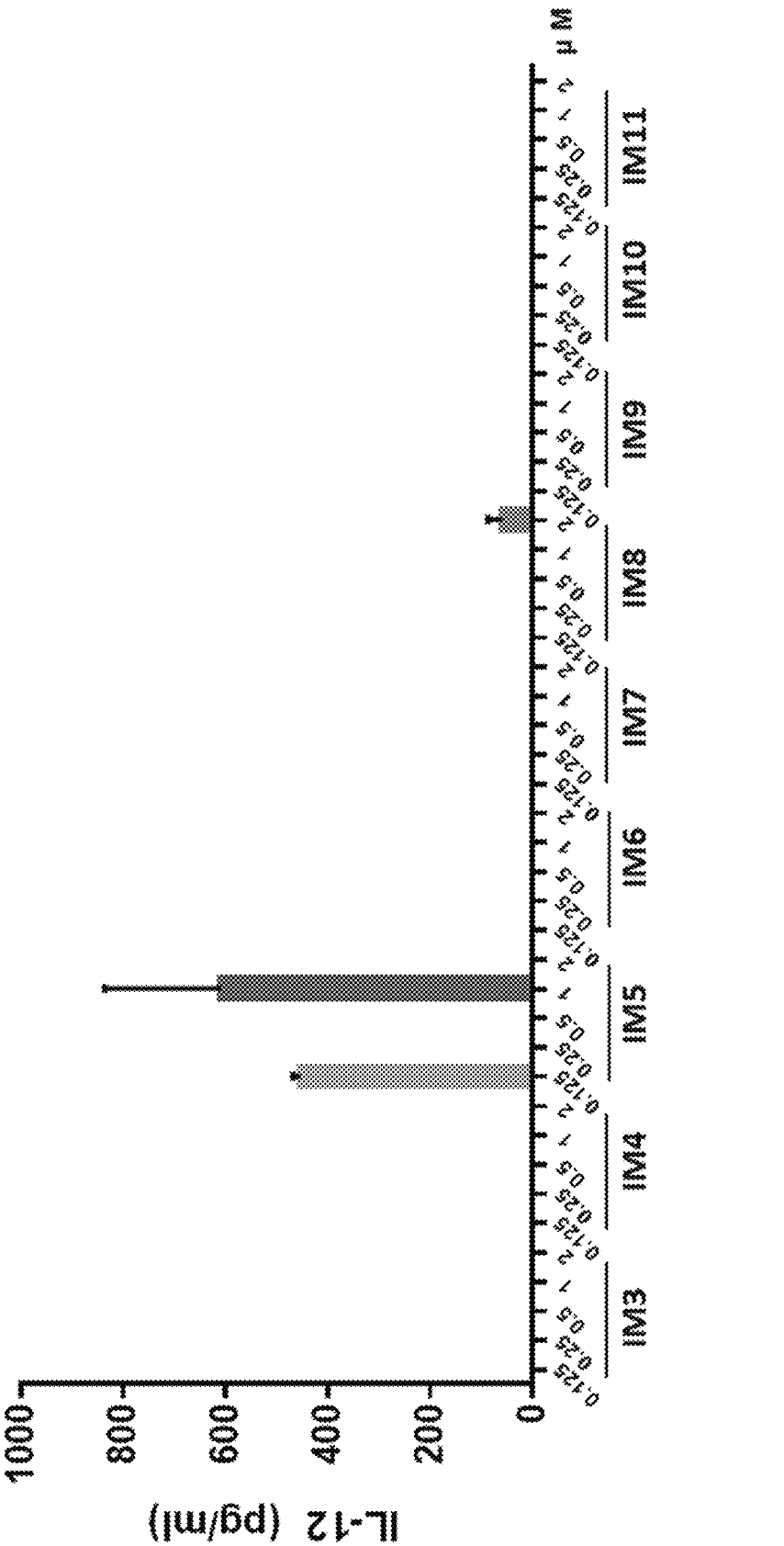
FIG. 6 and FIG. 7 are results of an ability of a nucleotide fragment including a nucleotide sequence of SEQ ID NO. 3 or SEQ ID NO. 6 to 19 in stimulating IL-12 secretion.
Figure 7:
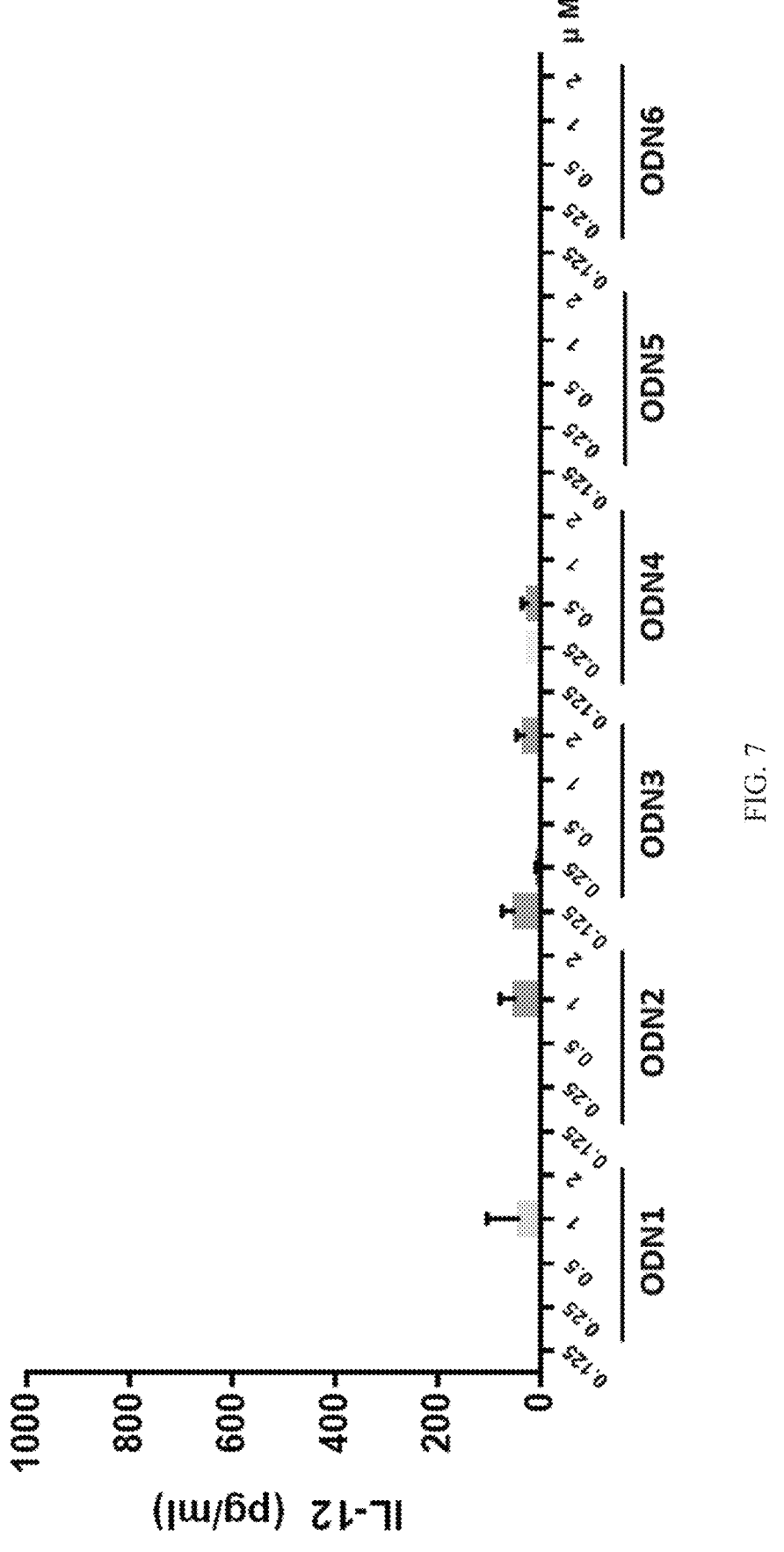

If the expression levels of IFN-γ and IL-12 were increased, it means that the strain has the ability to resist allergies and enhance immunocompetence. The results are shown in FIG. 2 and FIG. 3. According to the comparison results (FIG. 2 and FIG. 3), GM-080 shows the optimal ability in stimulating the expression of IFN-γ and IL-12. This result indicates that GM-080 has excellent ability in modulating immune function.

Embodiment 3: Analysis of the Ability of
Modulating Immune Function of Nucleotide
Fragments Containing ISS-ODNs Sequence Nucleotide fragments with SEQ ID NO. 3 or SEQ ID NO. 6-19 sequences were synthesized using a conventional method, respectively.

The mouse spleen was dissociated into single-cell suspensions of spleen cells based on a conventional method. The spleen cells were added into a 96-well plate (100 μl per well) at a concentration of $4 \times 10^6$ cells/ml, and then each of the to-be-tested ISS-ODNs nucleotide fragment was added into a 96-well plate (100 μl per well) at a concentration of 2, 1, 0.5, 0.25, or 0.125 μM. 100 μl of culture medium was used as the blank control group (mock), 100 μl of 2 μg/ml LPS (lipopolysaccharide) was used as the positive control group-1, and 100 μl of 4 μg/ml conA (concanavalin A) was used as the positive control group-2. After 48 hours of cultivation, the treated spleen cells were centrifuged and the supernatants were collected for IFN-γ and IL-12 analysis using the commercially available kits (BD OptEIA™ Mouse IFN-γ ELISA Set, Cat: 555138; BD OptEIA™ Mouse IL-12 (p70) ELISA Set, Cat: 555256).

The results are shown in FIGS. 4 to 7. The nucleotide fragments with ODN2, ODN3 or ODN5 sequence exhibit the abilities in stimulating spleen cells to produce IFN-γ, and the nucleotide fragment with ODN2 sequence shows the optimal ability that it is capable of stimulating spleen cells to produce approximately 490±272.74 μg/ml IFN-γ. In addition, the nucleotide fragments with IM5, IM8, ODN1, ODN2, ODN3 or ODN4 sequence exhibit the abilities in stimulating spleen cells to produce IL-12, and the nucleotide fragment with IM5 sequence shows the optimal ability that it is capable of stimulating spleen cells to produce approximately 453.5±15.55~609.8±227.69 pg/ml IL-12.

Embodiment 4. Preparation of Extracellular
Vesicles (EVs) of *Lactobacillus paracasei*

The overnight cultured medium of GM-080 or BCRC 16100 was centrifuged (3000 g, 5 min) to remove the bacterial cells, and the supernatant was collected and filtered with a 0.22 μm filter membrane (Pall Corporation, Cat. No. PN 4612). Subsequently, extracellular vesicles were isolated from the filtered supernatant through repeated filtering and concentrating the filtered supernatant with a 100 kDa NMWL ultrafiltration membrane (Millipore, Cat. No. UFC510008) under the conditions of centrifugal force 14000 g for 10 minutes. After 6 ml of the supernatant was concentrated to 100 μl, the concentrated supernatant was washed for two times with 0.5 ml of PBS each time to obtain the extracellular vesicles. The obtained extracellular vesicles were then stored at –20° C. The particle diameter and the particle concentration of the extracellular vesicles were analyzed with a particle size analyzer (Nanoparticle tracking analysis, NTA; NanoSight NS300, NanoSight Ltd., Amesbury, UK) and the protein concentration was quantified. The images of the extracellular vesicles were taken by a transmission electron microscope (TEM; JEM-1400, JEOL Ltd., Tokyo, Japan).

Figure 8:
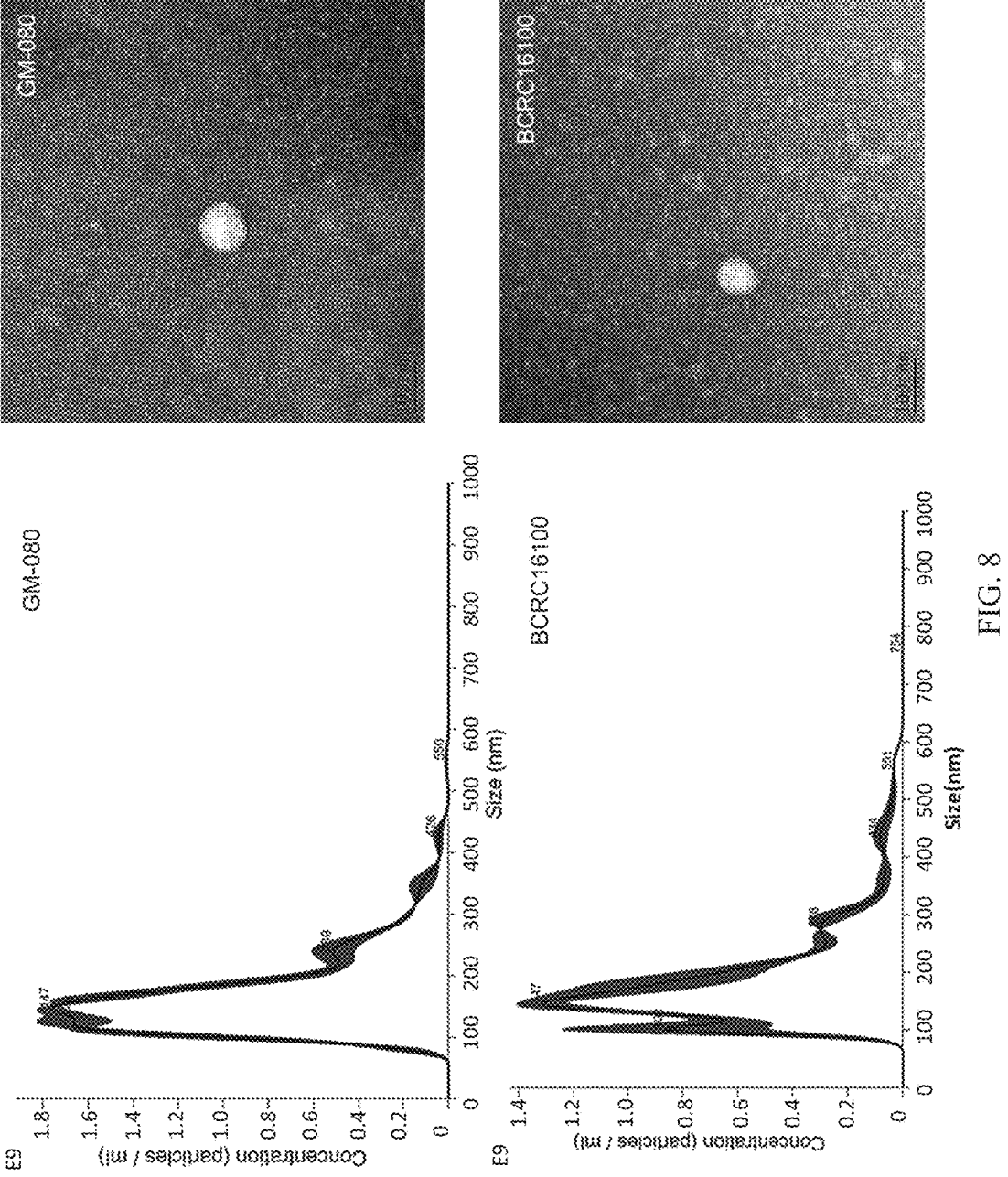
FIG. 8 is a size and characteristics of an extracellular vesicle of the *Lactobacillus paracasei* GM-080 and the *Lactobacillus paracasei* BCRC 16100.

The results are shown in FIG. 8. The diameter of the extracellular vesicles of GM-080 and BCRC 16100 is about 100 to 300 nm, the average diameter of the extracellular vesicles of GM-080 is 175.1±2 nm; the average diameter of the extracellular vesicles of BCRC 16100 is 202.9±10.4 nm.

The observed results of TEM accord with the above diameter results determined by the NTA.

Embodiment 5: Analysis the Abilities of
Extracellular Vesicles (EVs) of the *Lactobacillus paracasei* GM-080 in Modulating Immune
Function and Anti-Inflammatory Modulate immune function analysis was performed as follows. The mouse spleen was dissociated into single-cell suspensions of spleen cells base on conventional methods. The spleen cells were added into a 96-well plate (100 μl per well) at a concentration of $4 \times 10^6$ cells/ml, and then the extracellular vesicles of GM-080 as prepared in Embodiment 4 were added into the 96-well plate (100 μl per well) at a concentration of 0.01~0.0001 μg/ml. The extracellular vesicle of BCRC 16100 was used as a comparison example, 100 μl of culture medium was used as the blank control group (mock), 100 μl of 2 μg/ml LPS (lipopolysaccharide) was used as the positive control group-1, and 100 μl of 4 μg/ml conA (concanavalin A) was used as the positive control group-2. After 48 hours of cultivation, the treated spleen cells were centrifuged and the supernatant was collected for IFN-γ and IL-12 analysis using the commercially available kits (BD OptEIA™ Mouse IFN-γ ELISA Set, Cat: 555138; BD OptEIA™ Mouse IL-12 (p70) ELISA Set, Cat: 555256).

Anti-inflammatory analysis was performed as follows. RAW264.7 cells were added into a 24-well plate (final cell number: $4 \times 10^5$ cells/well). After incubated overnight at 37° C., the RAW264.7 cells were washed with PBS once and incubated with a serum-free DMEM culture medium for 2 hours. 100 μl of extracellular vesicles of GM-080 (1~0.001 μg/ml) as prepared in Embodiment 4 were subsequently added into the 24-well plate. After 2 hours, 0.5 ml of DMEM culture medium containing 200 ng/ml LPS was added into the 24-well plate (the final concentration of the extracellular vesicles is 0.1~ 0.0001 μg/ml) and the extracellular vesicle of BCRC 16100 was used as a comparative example, and 0.5 ml DMEM was used as the control group (mock). After 20 hours of coincubation, the supernatant of the cells was collected to determine the level of nitric oxide (NO). 80 ul of the supernatant was mixed with the commercially available NO reagents (80 ul Griess reagent A+80 ul Griess reagent B), and after 5 minutes reaction at room temperature, the absorbance of the mixture at OD550 nm was measured using an ELISA reader.

Figure 9:
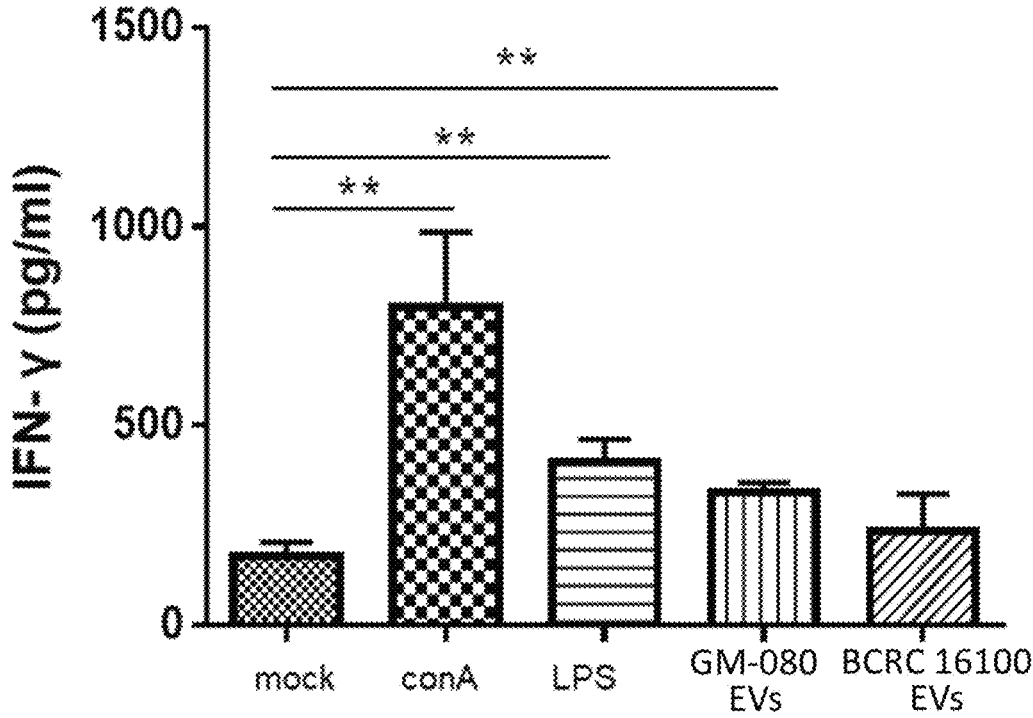
FIG. 9 is results of an ability of the extracellular vesicle of the *Lactobacillus paracasei* GM-080 and the *Lactobacillus paracasei* BCRC 16100 in stimulating IFN-γ secretion.
Figure 10:
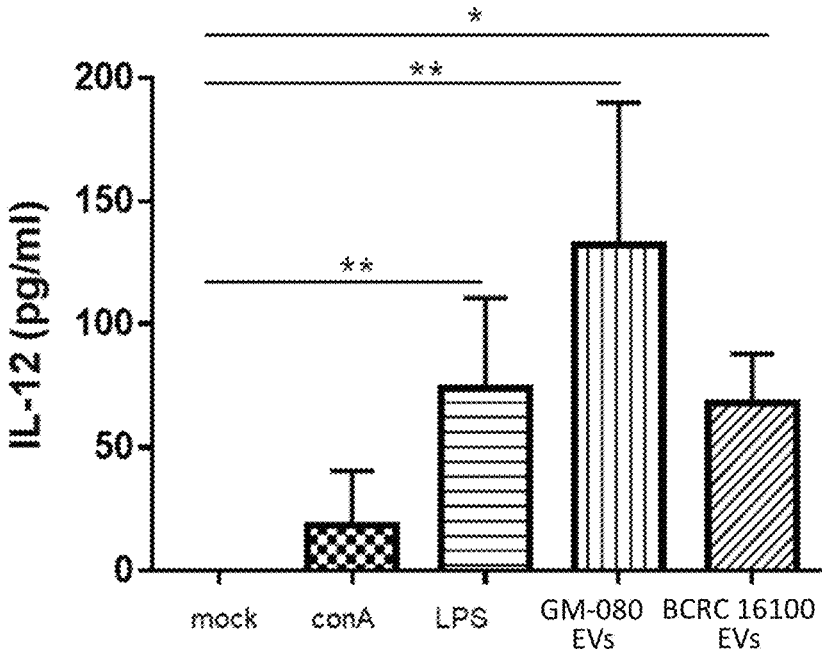
FIG. 10 is results of an ability of the extracellular vesicle of the *Lactobacillus paracasei* GM-080 and the *Lactobacillus paracasei* BCRC 16100 in stimulating IL-12 secretion.
Figure 11:
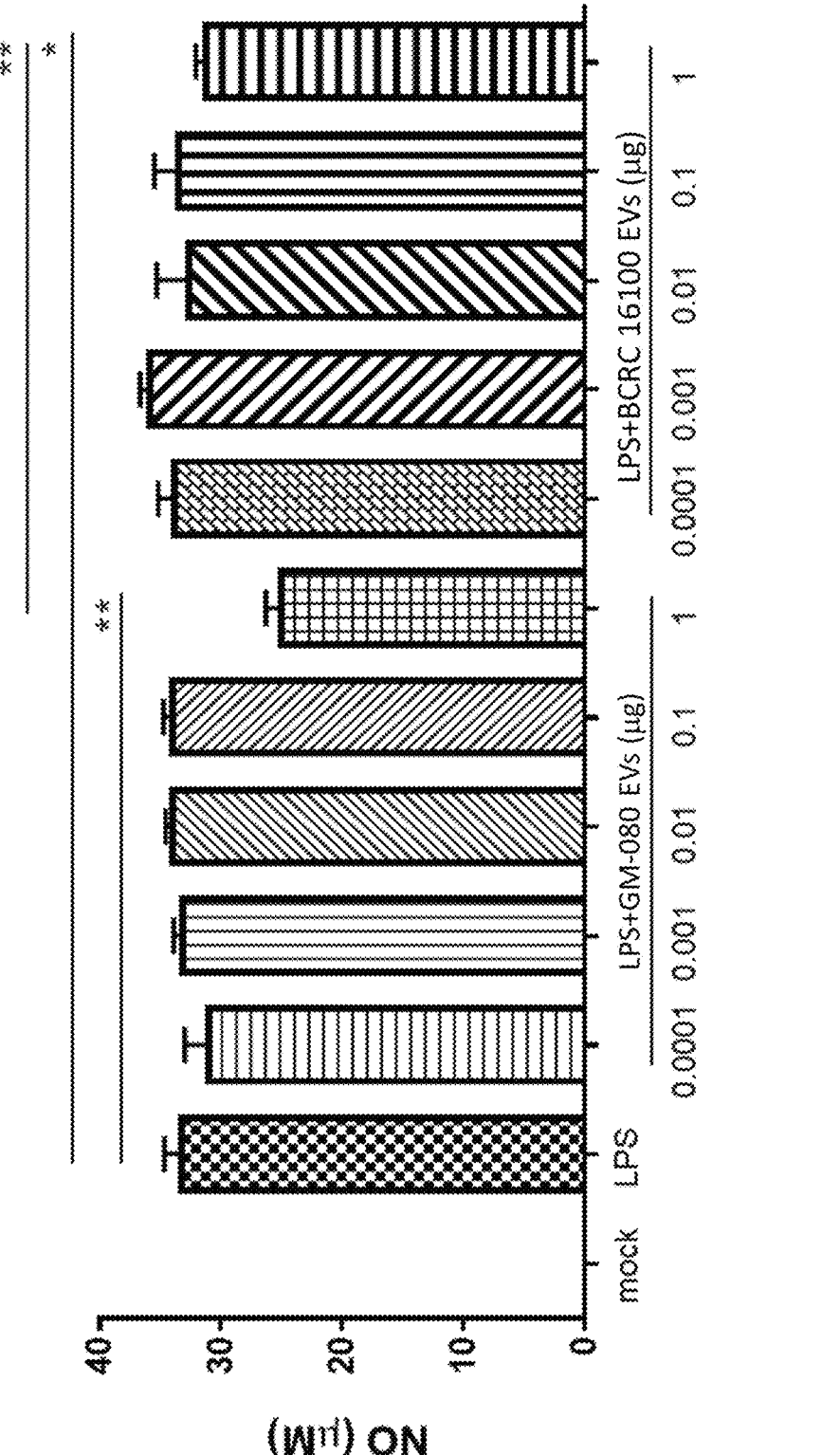
FIG. 11 is results of an anti-inflammatory ability of the extracellular vesicle of the *Lactobacillus paracasei* GM-080 and the *Lactobacillus paracasei* BCRC 16100.

The results are shown in FIG. 9 to FIG. 11. From the results of FIG. 9, it can be found that the extracellular vesicle of GM-080 is able to stimulate the secretion of IFN-γ even at a low concentration (0.0001 μg/ml), while the extracellular vesicle of BCRC 16100 dose not significantly increase the secretion of IFN-γ. From the results of FIG. 10, it can be found that the extracellular vesicles of GM-080 and BCRC 16100 at a medium concentration (0.01 μg/ml) both can stimulate the secretion of IL-12, but the extracellular vesicles of GM-080 exhibits a higher stimulating ability. In addition, from the results of FIG. 10, it can be found that the extracellular vesicle of GM-080 at a high concentration (1 μg/ml) inhibits the production of nitric oxide (NO) caused by LPS. The results indicate that the extracellular vesicle of GM-080 has the ability to inhibit the inflammatory response caused by LPS, therefore, it is beneficial to inhibit the depravation of allergic diseases.

After summarizing the above results, it can be known that:

1) In comparison with other *Lactobacillus paracasei* strains, the *Lactobacillus paracasei* GM-080 has a better ability in modulating immune function.

2) The extracellular vesicle of the *Lactobacillus paracasei* GM-080 is capable of effectively stimulating the secretion of IFN-γ and IL-12, increasing the expression level of IFN-γ and IL-12, and inhibiting the nitric oxide (NO) production caused by LPS. The results show that the extracellular vesicle of the *Lactobacillus paracasei* GM-080 is capable of inhibiting allergic reactions.

3) In addition, the nucleotide fragment comprising a nucleotide sequence of SEQ ID NO. 7, SEQ ID NO. 10, SEQ ID NO. 14, SEQ ID NO. 15, SEQ ID NO. 16, SEQ ID NO. 17 or SEQ ID NO. 18 has an efficacy of stimulating the secretion of IFN-γ or IL-12.

Accordingly, the *Lactobacillus paracasei* GM-080, the extracellular vesicle and the nucleotide fragment thereof provided by the invention are very suitable for using in the development and preparation of compositions for modulating immune function, including anti-inflammatory or anti-allergic composition. The invention provides more options for allergy sufferers and contributes to the development of the industry and products used for modulating immune function.

For the content disclosed in the preferred embodiments of this specification, a person having ordinary in the art to which the invention pertains can clearly know that the foregoing embodiments are only for exemplifying; a person having ordinary in the art to which the invention pertains can implement it through many changes and substitutions without differing from the technical features of the invention. According to the embodiments of the specification, the invention can have many variations without hindering its implementation. The appended claims provided in this specification define the scope of the invention, the scope covers the aforementioned methods and structures and their equivalent inventions.

The above-mentioned multiple efficacies fully meet the statutory patent requirements of novelty and non-obviousness, and therefore the application is submitted in accordance with the laws, and the Office is earnestly requested to grant the application for this utility patent to encourage invention.

Many changes and modifications in the above described embodiments of the invention can, of course, be carried out without departing from the scope thereof. Accordingly, to promote the progress in science and the useful arts, the invention is disclosed and is intended to be limited only by the scope of the appended claims.

What is claimed is:

1. A method for immunomodulation for anti-allergic or anti-inflammatory effect by stimulating the secretion of IFN-γ or IL-12, comprising administering to a subject in need thereof a therapeutically effective amount of a composition including a nucleotide which sequence is SEQ ID NO. 7, SEQ ID NO. 15, SEQ ID NO. 16, or SEQ ID NO. 18;

wherein SEQ ID NO. 15 and SEQ ID NO. 18 stimulate the secretion of IFN-γ;

wherein SEQ ID NO. 7 and SEQ ID NO. 16 stimulate the secretion of IL-12.

2. The method as claimed in claim 1, wherein the dosage of the nucleotide is 0.125 μM.

\* \* \* \* \*

SEQUENCE LISTING

```
<160> NUMBER OF SEQ ID NOS: 19

<210> SEQ ID NO 1
<211> LENGTH: 6
<212> TYPE: DNA
<213> ORGANISM: Lactobacillus paracasei

<400> SEQUENCE: 1 ttaggg                                                        6

<210> SEQ ID NO 2
<211> LENGTH: 8
<212> TYPE: DNA
<213> ORGANISM: Lactobacillus paracasei

<400> SEQUENCE: 2 tttcgttt                                                      8

<210> SEQ ID NO 3
<211> LENGTH: 10
<212> TYPE: DNA
<213> ORGANISM: Lactobacillus paracasei

<400> SEQUENCE: 3
tcaagcttga                                                   10

<210> SEQ ID NO 4
<211> LENGTH: 10
<212> TYPE: DNA
<213> ORGANISM: Lactobacillus paracasei

<400> SEQUENCE: 4
gacgatcgtc                                                   10

<210> SEQ ID NO 5
<211> LENGTH: 10
<212> TYPE: DNA
<213> ORGANISM: Lactobacillus paracasei
```

<400> SEQUENCE: 5
acgacgtcgt                                                              10

<210> SEQ ID NO 6
<211> LENGTH: 20
<212> TYPE: DNA
<213> ORGANISM: Artificial Sequence
<220> FEATURE:
<223> OTHER INFORMATION: A synthetic sequence contains sequence IM3, as
      a core sequence.

<400> SEQUENCE: 6
caagcgtcaa gcttgaatga                                                   20

<210> SEQ ID NO 7
<211> LENGTH: 20
<212> TYPE: DNA
<213> ORGANISM: Artificial Sequence
<220> FEATURE:
<223> OTHER INFORMATION: A synthetic sequence contains sequence IM3, as
      a core sequence.

<400> SEQUENCE: 7
aaaaattcaa gcttgatagt                                                   20

<210> SEQ ID NO 8
<211> LENGTH: 20
<212> TYPE: DNA
<213> ORGANISM: Artificial Sequence
<220> FEATURE:
<223> OTHER INFORMATION: A synthetic sequence contains sequence IM3, as
      a core sequence.

<400> SEQUENCE: 8
ccatcgtcaa gcttgacttg                                                   20

<210> SEQ ID NO 9
<211> LENGTH: 20
<212> TYPE: DNA
<213> ORGANISM: Artificial Sequence
<220> FEATURE:
<223> OTHER INFORMATION: A synthetic sequence contains sequence IM3, as
      a core sequence.

<400> SEQUENCE: 9
ccctaatcaa gcttgattaa                                                   20

<210> SEQ ID NO 10
<211> LENGTH: 20
<212> TYPE: DNA
<213> ORGANISM: Artificial Sequence
<220> FEATURE:
<223> OTHER INFORMATION: A synthetic sequence contains sequence IM3, as
      a core sequence.

<400> SEQUENCE: 10
gcagcttcaa gcttgaaaaa                                                   20

<210> SEQ ID NO 11
<211> LENGTH: 20
<212> TYPE: DNA
<213> ORGANISM: Artificial Sequence
<220> FEATURE:
<223> OTHER INFORMATION: A synthetic sequence contains sequence IM3, as
      a core sequence.

```
<400> SEQUENCE: 11
ccggcctcaa gcttgaattg                                                    20

<210> SEQ ID NO 12
<211> LENGTH: 20
<212> TYPE: DNA
<213> ORGANISM: Artificial Sequence
<220> FEATURE:
<223> OTHER INFORMATION: A synthetic sequence contains sequence IM3, as
      a core sequence.

<400> SEQUENCE: 12
tttcattcaa gcttgacgct                                                    20

<210> SEQ ID NO 13
<211> LENGTH: 20
<212> TYPE: DNA
<213> ORGANISM: Artificial Sequence
<220> FEATURE:
<223> OTHER INFORMATION: A synthetic sequence contains sequence IM3, as
      a core sequence.

<400> SEQUENCE: 13
ccttaatcaa gcttgattag                                                    20

<210> SEQ ID NO 14
<211> LENGTH: 20
<212> TYPE: DNA
<213> ORGANISM: Artificial Sequence
<220> FEATURE:
<223> OTHER INFORMATION: A synthetic sequence contains sequence ODN2216,
      as a core sequence.

<400> SEQUENCE: 14
gcttgacgat cgtctctgga                                                    20

<210> SEQ ID NO 15
<211> LENGTH: 21
<212> TYPE: DNA
<213> ORGANISM: Artificial Sequence
<220> FEATURE:
<223> OTHER INFORMATION: A synthetic sequence contains sequence ODN2336,
      as a core sequence.

<400> SEQUENCE: 15
ggtcacgacg tcgtttacaa a                                                  21

<210> SEQ ID NO 16
<211> LENGTH: 20
<212> TYPE: DNA
<213> ORGANISM: Artificial Sequence
<220> FEATURE:
<223> OTHER INFORMATION: A synthetic sequence contains sequence ODN2216,
      as a core sequence.

<400> SEQUENCE: 16
aattgacgat cgtctaattc                                                    20

<210> SEQ ID NO 17
<211> LENGTH: 20
<212> TYPE: DNA
<213> ORGANISM: Artificial Sequence
<220> FEATURE:
<223> OTHER INFORMATION: A synthetic sequence contains sequence ODN2216,
      as a core sequence.

<400> SEQUENCE: 17
```

-continued

```
tgtcgacgat cgtcgtctgt                                              20

<210> SEQ ID NO 18
<211> LENGTH: 20
<212> TYPE: DNA
<213> ORGANISM: Artificial Sequence
<220> FEATURE:
<223> OTHER INFORMATION: A synthetic sequence contains sequence ODN2216,
      as a core sequence.

<400> SEQUENCE: 18
cagagacgat cgtcaagcga                                              20

<210> SEQ ID NO 19
<211> LENGTH: 21
<212> TYPE: DNA
<213> ORGANISM: Artificial Sequence
<220> FEATURE:
<223> OTHER INFORMATION: A synthetic sequence contains sequence ODN2336,
      as a core sequence.

<400> SEQUENCE: 19
cgtcacgacg tcgtgaccgg c                                            21
```